(12) United States Patent
Pernthaler et al.

(10) Patent No.: US 7,736,855 B2
(45) Date of Patent: Jun. 15, 2010

(54) PROCESS FOR SEPARATING MICROORGANISMS

(75) Inventors: Annelie Pernthaler, Pasadena, CA (US); Victoria J. Orphan, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 612 days.

(21) Appl. No.: 11/746,374

(22) Filed: May 9, 2007

(65) Prior Publication Data

US 2007/0292937 A1    Dec. 20, 2007

Related U.S. Application Data

(60) Provisional application No. 60/800,092, filed on May 12, 2006.

(51) Int. Cl.
*C12Q 1/68* (2006.01)
*C12N 1/00* (2006.01)

(52) U.S. Cl. ............. 435/6; 435/7.1; 435/243

(58) Field of Classification Search ............ None
See application file for complete search history.

(56) References Cited

OTHER PUBLICATIONS

Yeung, Yik A. et al.; Biotechnology Progress, vol. 18, (Apr. 2002), pp. 212-220.
Neuman, Keir C. et al.; Review of Scientific Instruments, vol. 75, (Sep. 2004), pp. 2787-2809.
Kalyuzhnaya, Marina G. et al.; Applied & Environmental Microbiology, vol. 72, (Jun. 2006), pp. 4293-4301.
Sekar, Raju et al.; Applied & Environmental Microbiology, vol. 70, (Oct. 2004), pp. 6210-6219.
Wallner, Gunter et al.; Applied and Environmental Microbiology, vol. 63, (Nov. 1997), pp. 4223-4231.
Pernthaler, Annelie et al.; Applied & Environmental Microbiology, vol. 68, (Jun. 2002), pp. 3094-3101).
Schippers, Axel et al.; Nature, vol. 433, (Feb. 2005), pp. 861-864.
Pernthaler, Annelie et al.; "Simultaneous fluorescence in situ hybridization of mRNA and rRNA for the detection of gene expression in environmental microbes." in: Leadbetter, J.R. (ed)., Methods in Enzymology (San Diego: Elsevier, 2005), pp. 352-371.
Stoffels et al.; Environmental Microbiology, vol. 1, (Mar. 1999), pp. 259-271.
Lu Huachang, et al.; Journal of Materials Chemistry, Vo. 14, (Mar. 2004) pp. 1336-1341.
Liang, Sheng et al.; Journal of Radioanalytical and Nuclear Chemistry, vol. 269, (Jan. 2006), pp. 3-7.
Lucocq, John; Microscopy Research and Technique, vol. 35, (1996), pp. 314-319.
Dynal; Surface Activated Dynabreads for Cell Separation, Downloaded from internet; (2 pages) (2005).
Dynal; Dynabeads Pan House IgG, Downloaded from internet; (2 pages) (2007).
Applied & Environmental Microbiology, vol. 71, (Jan. 2005), pp. 467-479, Knittel et al.
Sekar, Raju et al.; Applied & Environmental Microbiology, vol. 69, (May 2003), pp. 2928-2935.
Zwirglmaier, K. et al.; Applied & Environmental Microbiology, vol. 70, (Jan. 2004), pp. 494-497.
Pernthaler, Annelie et al.; "Sensitive multi-color fluorescence in situ hybridization for the identification of environmental microorganisms" in Molecular Microbial Ecology Manual. Second Edition (Kluwer 2004). pp. 1-15.
Van Heusden, Jimmy et al.; The Journal of Histochemistry & Cytochemistry, vol. 45, (1997), pp. 315-319.
Pernthaler, Annelie et al.; Applied & Environmental Microbiology, vol. 68, (Jun. 2002), pp. 3094-3101.

*Primary Examiner*—James Martinell
(74) *Attorney, Agent, or Firm*—Milstein Zhang & Wu LLC; Joseph B. Milstein (57) ABSTRACT

Disclosed in this specification is a process for separating a microorganism from a sample by selectively hybridizing the microorganism's nucleic acid with a labeled probe. Suitable labels include antigens as well an enzymes. In one embodiment, an antigen is introduced to the sample which is activated by the enzyme. The labeled microorganism is then exposed to a substrate that is coated with an antibody which is specific to the activated antigen, thus binding the labeled microorganism to the substrate. The substrate may be, for example, a magnetic substrate such as a paramagnetic bead.

45 Claims, 5 Drawing Sheets

PROCESS FOR SEPARATING MICROORGANISMS

CROSS-REFERENCE TO RELATED APPLICATION

This application claims priority from co-pending U.S. provisional application Ser. No. 60/800,092, filed May 12, 2006, which application is hereby incorporated by reference in its entirety into this specification.

STATEMENT REGARDING FEDERALLY SPONSORED RESEARCH

The invention described herein was made in the performance of work under National Science Foundation Grant No. MCB-0398596, and is subject to the provisions of Public Law 96-517 (35 U.S.C. §202) in which the Contractor has elected to retain title.

FIELD OF THE INVENTION

This invention relates, in one embodiment, to a process for separating a group of microorganisms from a sample. The sample is exposed to a probe that hybridizes to a nucleic acid of the group of microorganisms. An antibody, which is specific to the probe, is then used to bind the hybridized organism to a substrate. In this manner, a group of microorganisms may be selectively separated from the sample.

BACKGROUND OF THE INVENTION

It has been a longstanding objective in the art to be able to separate a specific group of microorganisms from a sample. Traditionally, a sample that contains a plurality of microorganisms is diluted and applied to a nutrient rich culture media. Due to the high dilution of the original sample, individual microorganisms are effectively isolated from other microorganisms that were also present in the sample. Over time, colonies of bacteria grow on the media—each colony originating from one of the individual microorganisms. Since each colony shares the same progenitor, such colonies contain only a single type of microorganism. Such colonies may be collected and used to generate substantial quantities of essentially pure microorganisms.

For such a technique to function, the microorganism must be culturable. For reasons that are not clear, the vast majority of microorganisms fail to grow when they are removed from their natural environment. It appears that there is a synergistic relationship between many neighboring species of microorganisms that prevents many species of microorganism from being cultured in isolation. This is a matter of great concern for microbiologists. Often, a scientist wishes to generate antibodies that are specific to a given species of microorganism. However, when the scientist is unable to isolate the microorganism from its environment, the scientist is unable to generate such antibodies.

Cell enrichment/purification approaches have been reported in the literature, but all have significant limitations which hinder their successful application to uncultured microorganisms. Immunomagnetic separation has been shown to be an efficient and sensitive method for the enrichment and isolation of cells in a wide variety of medical and food samples and few environmental samples. See Biotechnology Progress, Vol. 18, (April, 2002), pp. 212-220. In this technique, paramagnetic beads coated with antibodies specific to surface antigens of the target cells are used to label these cells and subsequently separate them from unlabelled cells in a magnetic field. While effective in the medical field, a significant drawback of this method is the requirement for antibodies that are specific to the target organisms. Production of such specific antibodies requires a pure sample of the organism itself. Such pure samples are often not available using conventional techniques.

Optical trapping and manipulation of bacterial cells and viruses with infrared lasers can be applied to collect individual cells. However, this method is time consuming and gives only a small amount of cellular material for analysis. See *Review of Scientific Instruments*, Vol. 75, (September, 2004), pp. 2787-2809.

Flow cytometry is another method that has been applied to enrich cells. To date, the inventor is aware of only one report showing the enrichment of hybridized bacteria from sediment using flow cytometry. Such a technique is illustrated in a paper to Kalyuzhnaya et al. See *Applied & Environmental Microbiology*, Vol. 72, (June, 2006), pp. 4293-4301. Kalyuzhnaya et al. enriched hybridized Type I and Type II methanotrophs from Lake Washington sediment. Abundances of target cells in lake sediment samples were 4.7% (percent of total cell counts, Type I methanotrophs) and 1.2% (Type II methanotrophs). After flow cytometric sorting, Type I methanotrophs comprised 59% of the clone library (no cell counts were performed) and Type II methanotrophs counted 47.5%. Another report (*Applied & Environmental Microbiology*, Vol. 70, (October, 2004), pp. 6210-6219) shows sorting of bacterial groups from plankton after CARD-FISH with purities ranging from 96% to 97%. Flow sorting of activated-sludge microorganisms, hybridized with fluorescein labeled oligonucleotide probes, has been reported by Wallner et al., (*Applied and Environmental Microbiology*, Vol. 63, (November, 1997), pp. 4223-4231. Here, *Acinetobacter* was enriched from 0.3 to 0.6% total abundance in the original sample to 35 to 84% in the sorted fraction. Leptotrix was enriched from 12 to 13% in the original sample to 69 to 82% in the sorted fraction.

Fluorescence in situ hybridization (FISH) is commonly used in microbial ecology studies to visualize microorganisms, most often directed toward the 16S rRNA. Until recently, FISH has been limited to the detection of highly expressed rRNA genes. To overcome this limitation, Pernthaler et al. (*Applied & Environmental Microbiology*, Vol. 68, (June, 2002), pp. 3094-3101) described an adaptation of FISH called CARD-FISH that uses fluorescently labeled tyramides as a substrate for the probe-delivered horseradish peroxidase. Using CARD-FISH the hybridization signal can be increased up to 1000-fold and even slow growing microbes from deep subsurface samples (*Nature*, Vol 433, (February, 2005), pp. 861-864) can be detected. This method has also recently been applied in a modified protocol for the FISH detection of messenger RNA. See Pernthaler, A., and Pernthaler, J. "Simultaneous fluorescence in situ hybridization of mRNA and rRNA for the detection of gene expression in environmental microbes." in: Leadbetter, J. R. (ed)., *Methods in Enzymology* (San Diego: Elsevier, 2005), pp. 352-371.

Complementary polyribonucleotide probes have been used in conjunction with paramagnetic substrates by Stoffels et al. to separate one species from an artificially produced mix of species (*Environmental Microbiology*, Vol. 1, (March, 1999), pp. 259-271). Stoffels et al., used polyribonucleotide probes of about 300 bases length, targeting a highly variable region in domain III of the 23S rRNA. The probes of Stoffels have significant limits when compared to oligonucleotide probes: (A) the database for 23S rRNA sequences is much smaller (about 20,000 sequences) than the 16S rRNA database (about 500,000 sequences), thus the possibility to design probes that cross-react with other species is relatively high; (B) the length of these probes complicates probe design; and (C) these probes are RNA probes, which makes them highly susceptible to degradation by RNases, which are present in every sample and every microbe and even survive fixation.

Therefore, a process for separating a desired group of microorganisms from a plurality of microorganisms is desired.

SUMMARY OF THE INVENTION

The invention comprises, in one form thereof, a process for separating a microorganism from a sample by selectively hybridizing the microorganism's nucleic acid with a labeled probe. Suitable labels include antigens as well an enzymes. In one embodiment, an antigen is introduced to the sample which is activated by the enzyme-label. The labeled microorganism is then exposed to a substrate that is coated with an antibody which is specific to the activated antigen, thus binding the labeled microorganism to the substrate. The substrate may be, for example, a magnetic substrate such as a paramagnetic bead.

In one aspect, the invention relates to a process for separating hybridized microorganisms from non-hybridized microorganisms. The process comprises the steps of: hybridizing a microorganism of a plurality of microorganisms with an enzyme-labeled probe that hybridizes to a nucleic acid of the microorganism, to produce hybridized microorganisms and non-hybridized microorganisms; exposing the hybridized microorganisms to an antigen that is activated by the enzyme to produce labeled microorganisms; exposing the labeled microorganisms to a substrate that is coated with an antibody specific to the antigen to produce a bound microorganism-substrate complex; and separating the bound microorganism-substrate complex from the non-hybridized microorganisms.

In one embodiment, the enzyme is a peroxidase. In one embodiment, the enzyme is a horseradish peroxidase. In one embodiment, the enzyme is a phosphatase. In one embodiment, the enzyme is selected from the group consisting of a glucose oxidase, a beta-galactosidase, and a urease.

In one embodiment, the process further comprises the step of pre-treating a raw sample which includes the plurality of microorganisms.

In one embodiment, the process further comprises the step of quenching an endogenous peroxidase.

In one embodiment, antigen is bound to a tyramide. In one embodiment, the antigen is a fluorescein. In one embodiment, the antigen is a biotin. In one embodiment, the antigen is a fluorescent dye. In one embodiment, the antigen is dinitrophenyl. In one embodiment, the antigen is digoxigenin.

In one embodiment, the nucleic acid is a ribonucleic acid. In one embodiment, the nucleic acid is a ribosomal ribonucleic acid. In one embodiment, the nucleic acid is a messenger ribonucleic acid. In one embodiment, the nucleic acid is a chromosomal nucleic acid. In one embodiment, the nucleic acid is a plasmid nucleic acid. In one embodiment, the nucleic acid is a viral nucleic acid.

In one embodiment, the substrate is a paramagnetic substrate. In one embodiment, the substrate is a magnetic substrate. In one embodiment, the substrate is a reaction tube.

In one embodiment, the probe is a DNA probe. In one embodiment, the probe is a single stranded DNA probe.

In a further aspect, the invention features a process for separating hybridized microorganisms from non-hybridized microorganisms. The process comprises the steps of: hybridizing a species of microorganisms of a plurality of microorganisms in a raw sample with a labeled, DNA probe that hybridizes to a nucleic acid of the species of microorganisms, to produce hybridized microorganisms and non-hybridized microorganisms; exposing the hybridized microorganisms to a substrate that is coated with an antibody specific to the label producing a bound microorganism-substrate complex; and separating the bound microorganism-substrate complex from the non-hybridized microorganisms.

In one embodiment, an endogenous peroxidase is present, and the process further comprises the step of quenching the endogenous peroxidase.

In one embodiment, the label is a fluorescein. In one embodiment, the label is a biotin. In one embodiment, the label is a fluorescent dye. In one embodiment, the label is dinitrophenyl. In one embodiment, the label is digoxigenin.

In one embodiment, the nucleic acid is a ribonucleic acid. In one embodiment, the nucleic acid is a ribosomal ribonucleic acid. In one embodiment, the nucleic acid is a messenger ribonucleic acid. In one embodiment, the nucleic acid is a chromosomal nucleic acid. In one embodiment, the nucleic acid is a plasmid nucleic acid. In one embodiment, the nucleic acid is a viral nucleic acid.

In one embodiment, the substrate is a paramagnetic substrate. In one embodiment, the substrate is a magnetic substrate. In one embodiment, the substrate is a reaction tube.

In one embodiment, the label is a fluorescein labeled tyramide and the process further comprises a second labeled probe which is a biotin labeled tyramide.

In one embodiment, the probe has from about 10 to about 200 base pairs. In one embodiment, the probe has from about 10 to about 100 base pairs.

In yet another aspect, the invention relates to a process for separating hybridized microorganisms from non-hybridized microorganisms. The process comprises the steps of: hybridizing a species of microorganisms of a plurality of microorganisms with an enzyme-labeled probe that hybridizes to a ribosomal ribonucleic acid of the species of microorganisms, to produce hybridized microorganisms and non-hybridized microorganisms; exposing the hybridized microorganisms to an antigen that is activated by the enzyme to produce labeled microorganisms; exposing the labeled microorganisms to a magnetic substrate that is coated with an antibody specific to the antigen to produce a bound microorganism-substrate complex; and separating the bound microorganism-substrate complex from the non-hybridized microorganisms.

In still a further aspect, the invention features a process for separating hybridized microorganisms from a sample. The process comprises the steps of: hybridizing a microorganism with an enzyme-labeled probe that hybridizes to a nucleic acid of the microorganism, to produce a hybridized microorganism; exposing the hybridized microorganism to an antigen that is activated by the enzyme to produce a labeled microorganism; exposing the labeled microorganism to a magnetic substrate that is coated with an antibody specific to the antigen to produce a bound microorganism-substrate complex; and separating the bound microorganism-substrate complex from the sample.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The examples set out herein illustrate several embodiments of the invention but should not be construed as limiting the scope of the invention in any manner The drawings are not necessarily to scale, emphasis instead generally being placed upon illustrating the principles of the invention. In the drawings, like numerals are used to indicate like parts throughout the various views. The present invention is disclosed with reference to the accompanying drawings, wherein:

DETAILED DESCRIPTION

Figure 1:
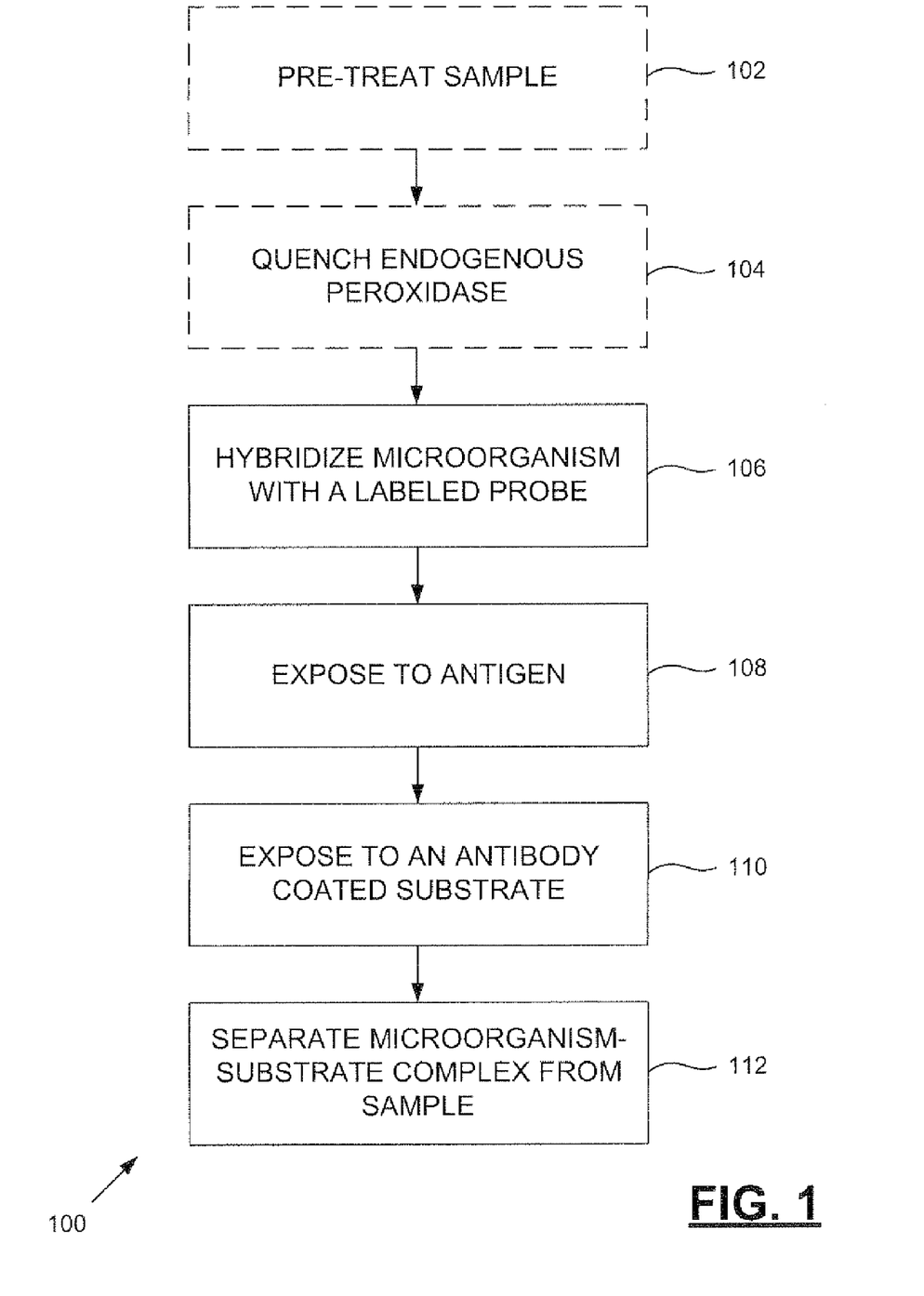
FIG. 1 is a flow diagram of one process of the invention.

FIG. 1 illustrates one process 100 of the invention. In step 102, which is optional, a raw sample is pre-treated. A raw sample from, for example, the bottom of a body of water often contains many microorganisms including bacteria, archaea, and viruses, as well as other organisms. The raw sample also contains detritus which further complicates treatment of the sample. Examples of pre-treatment steps that may be performed during the execution of step 102 include fixing of the microorganisms within the raw sample. Any suitable fixing technique may be used. For example, treatment of the raw sample with formaldehyde may fix the microorganisms. Other pre-treatment steps may include washes with suitable solutions. For example, washes may be performed using saline buffers such as phosphate-buffered saline (PBS). Other suitable solutions include aqueous ethanol solutions, trishydroxymethylaminomethane-hydrochloric acid (TrisHCl) solutions, ethylenediaminetetraacetic acid (EDTA) solutions, and pyrophosphate solutions. Sonication may also be used to assist in dispersing particulates. Centrifugation or filtering may also be used during pre-treatment step 102. Samples may be stored at reduced temperature (–20° C. to –80° C., for example).

In step 104 of process 100, which is also optional, certain endogenous enzymes are quenched. In some embodiments of the invention, these endogenous enzymes complicate subsequent steps of process 100. To avoid such a complication, it may be desirable to quench the enzymes in step 104. For example, it may be desirable to quench endogenous peroxidase enzymes by treating the sample with dilute hydrogen peroxide. In other embodiments, the presence of endogenous enzymes does not complicate subsequent steps, thus step 104 is unnecessary.

In step 106 of process 100, the sample is exposed to a labeled probe. The probe is a nucleic acid sequence designed to be complementary to a nucleic acid sequence within one group of microorganisms found within the sample. In one embodiment, the probe is a DNA probe, for example, a single stranded DNA probe. As known to those skilled in the art, such nucleic acid sequences may be selected to be species specific. Alternatively, such a probe may be selected to be specific to a group of microorganisms that belong to more than a single species. For example, a probe may be designed to be complementary to a chromosomal nucleic acid (deoxyribonucleic acid, DNA) sequence known to be found within the group of organisms to be isolated. Plasmid DNA or viral DNA may also be a suitable target. In another embodiment, the probe is designed to be complementary to a ribonucleic acid (RNA) sequence. For example, the RNA sequence may be a messenger RNA sequence (mRNA) or a ribosomal RNA sequence (rRNA). In one such embodiment, an rRNA sequence of the 16S portion of a ribosome is selected. For many microorganisms, such rRNA sequences are known, Reference databases are, for example, the Silva database (World Wide Web.arb-silva.de/), the Ribosomal Database Project (http://rdp.cme.msu.edu/), the National Centre for Biotechnology Information (World Wide Web.ncbi.nlm.nih-.gov/), and the European Bioinformatics Institute (World Wide Web.ebi.ac.uk/). Any suitable probe length may be used. In one embodiment, the probe contains from about 10 to about 200 nucleotides. In another embodiment, the probe contains from about 10 to about 100 nucleotides. In yet another embodiment, the probe contains from about 10 to about 40 nucleotides.

The labeled probe of step 106 includes both the probe, discussed above, and a label that is covalently bound to the probe. This label may be, for example, an enzyme (see FIG. 2) or an antigen (see FIG. 4).

Figure 2:
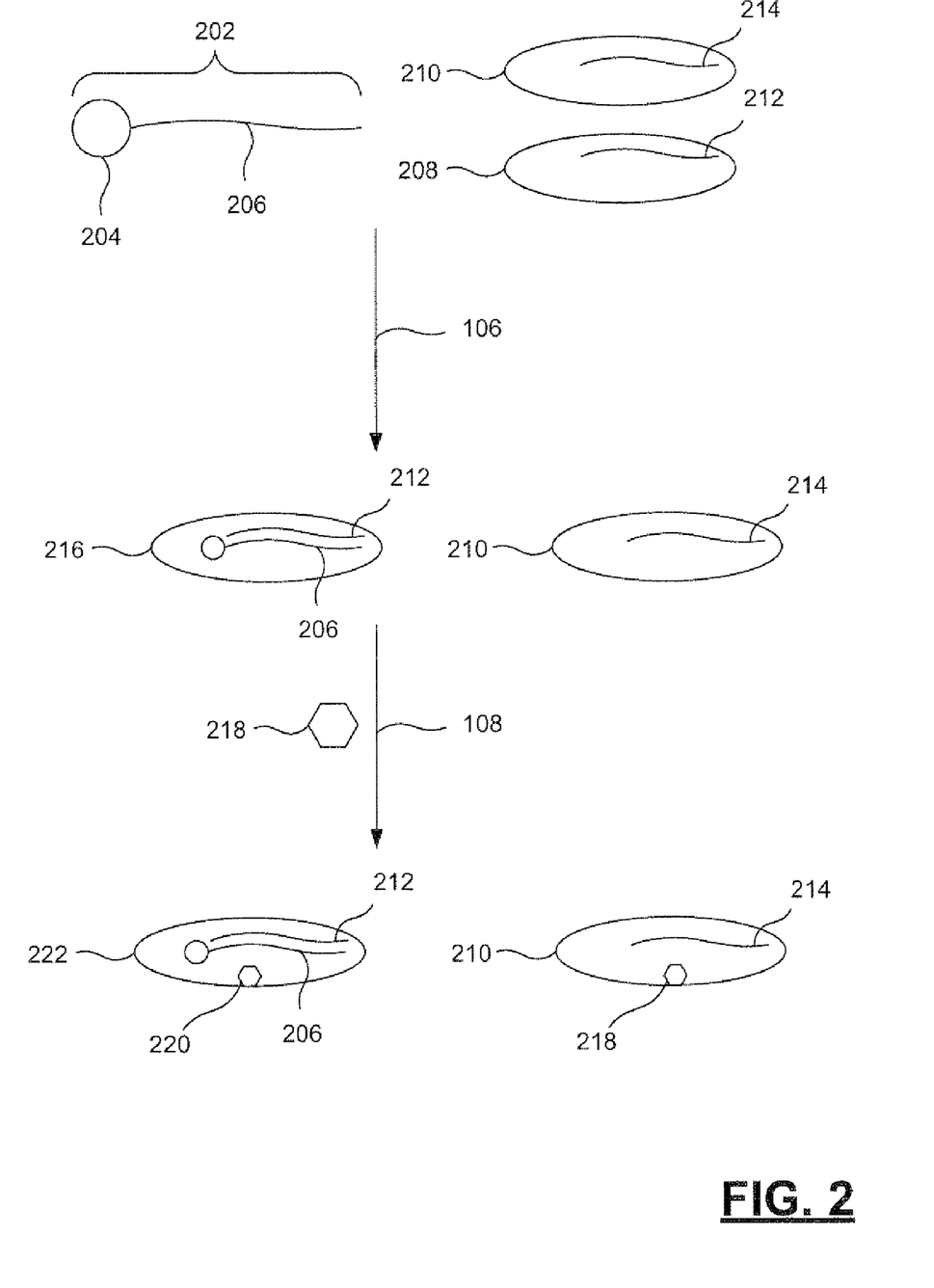
FIG. 2 is a graphic depiction of one embodiment of steps 106 and 108 of the present invention.

In one embodiment of step 106, shown in FIG. 2, the label is an enzyme. FIG. 2 depicts enzyme-labeled probe 202 which is comprised of enzyme 204 and probe 206, Enzyme labeled probe 202 is exposed to microorganisms 208 and 210. In the embodiment depicted in FIG. 2, microorganism 208 includes nucleic acid 212 and microorganism 210 includes nucleic acid 214. Probe 206 is complementary to nucleic acid 212, but is not complementary to nucleic acid 214. Upon exposure to microorganisms 208 and 210, enzyme labeled probe 202 hybridizes to nucleic acid 212, producing hybridized microorganism 216. Since nucleic acid 214 is not complementary to probe 206, microorganism 210 is not hybridized. Suitable enzymes for use as enzyme 204 include peroxidase enzymes, such as horseradish peroxidase, phosphatase enzymes, glucose oxidase enzymes, beta-galactosidase enzymes, and urease enzymes.

Once hybridized microorganism 216 is produced (see FIG. 2) the hybridized organism 216 is exposed to an antigen 218 (step 108, FIG. 1 and FIG. 2) that is activated by enzyme 204, thus producing labeled microorganism 222 that includes activated antigen 220. Since microorganism 210 was not hybridized, such a microorganism lacks enzyme 204. Thus microorganism 210 does not contain activated antigen 220. Suitable antigens include biotin, dinitrophenyl, digoxigenin, and fluorescent dyes, such as fluorescein. In another embodiment, the antigen is bound to another molecule, such as a tyramide. For example, a fluorescein antigen may be bound to a tyramide. Advantageously, CARD-FISH may be used in such an embodiment. Although not necessary for separation of the desired microorganisms, the use of fluorescent agents permits easy detection of the microorganism, and proved useful in demonstrating proof of principle (see Example 1).

Referring again to FIG. 1, and step 110 illustrated therein, once labeled microorganism 222 has been produced, the labeled microorganism 222 is exposed to a substrate that is coated with an antibody specific to the activated antigen. Such antibodies are commercially available and the techniques to coat substrates with such antibodies are widely known (for example: *Journal of Materials Chemistry*, Vo. 14, (March, 2004) pp. 1336-1341; *Journal of Radioanalytical and Nuclear Chemistry*, Vol. 269, (January, 2006), pp. 3-7; and *Microscopy Research and Technique*, Vol. 35, (1996), pp. 314-319. Suitable substrates include, for example, surfaces, such as the walls of a reaction tube or a lab card. In one embodiment, the substrate is a magnetic substrate. Suitable magnetic substrates include ferromagnetic, paramagnetic, and super-paramagnetic substrates. In one embodiment, the substrate is a bead. Suitable magnetic beads are, for example Dynabeads from Invitrogen Corporation, 1600 Faraday Avenue, PO Box 6482, Carlsbad, Calif. 92008. Magnets suitable for separating magnetic specimens from other materials are, for example, strong rare earth magnets (Dynal MPC, or magnetic particle concentrator, neodymium-iron-boron permanent magnets) available from Invitrogen Corporation. The labeled microorganisms 222, which contain the activated antigen 220, covalently binds to the antibody on the surface of the substrate producing a microorganism-substrate complex. In step 112, the microorganism-substrate complex is removed, thus separating the hybridized microorganisms from the non-hybridized microorganism. Depending on the nature of the substrate, various separation techniques may be used. For a magnetic substrate, a magnetic field may be used to remove the microorganism-substrate complex. Alternatively or additionally, simple filtering techniques may be used, since the resulting microorganism-substrate complex is larger than either the substrate or the microorganism individually.

Once the microorganism-substrate complex has been separated from the sample, the purified sample may be subjected to any number of post-processing steps. For example, the cells may be lysed and the resulting DNA or RNA may be subjected to nucleotide amplification techniques, such as polymerase chain reaction (PCR) or rolling circle amplification. Alternatively or additionally the microorganisms, although fixed, still present certain characteristic surface proteins to their environment. Antibodies may be generated which are specific to these surface proteins. Such antibodies may then be used to purify additional raw samples and extract that specific microorganism. In another embodiment, the teachings of this invention are used to isolate a specific cell line from a plurality of cell lines.

Figure 3:
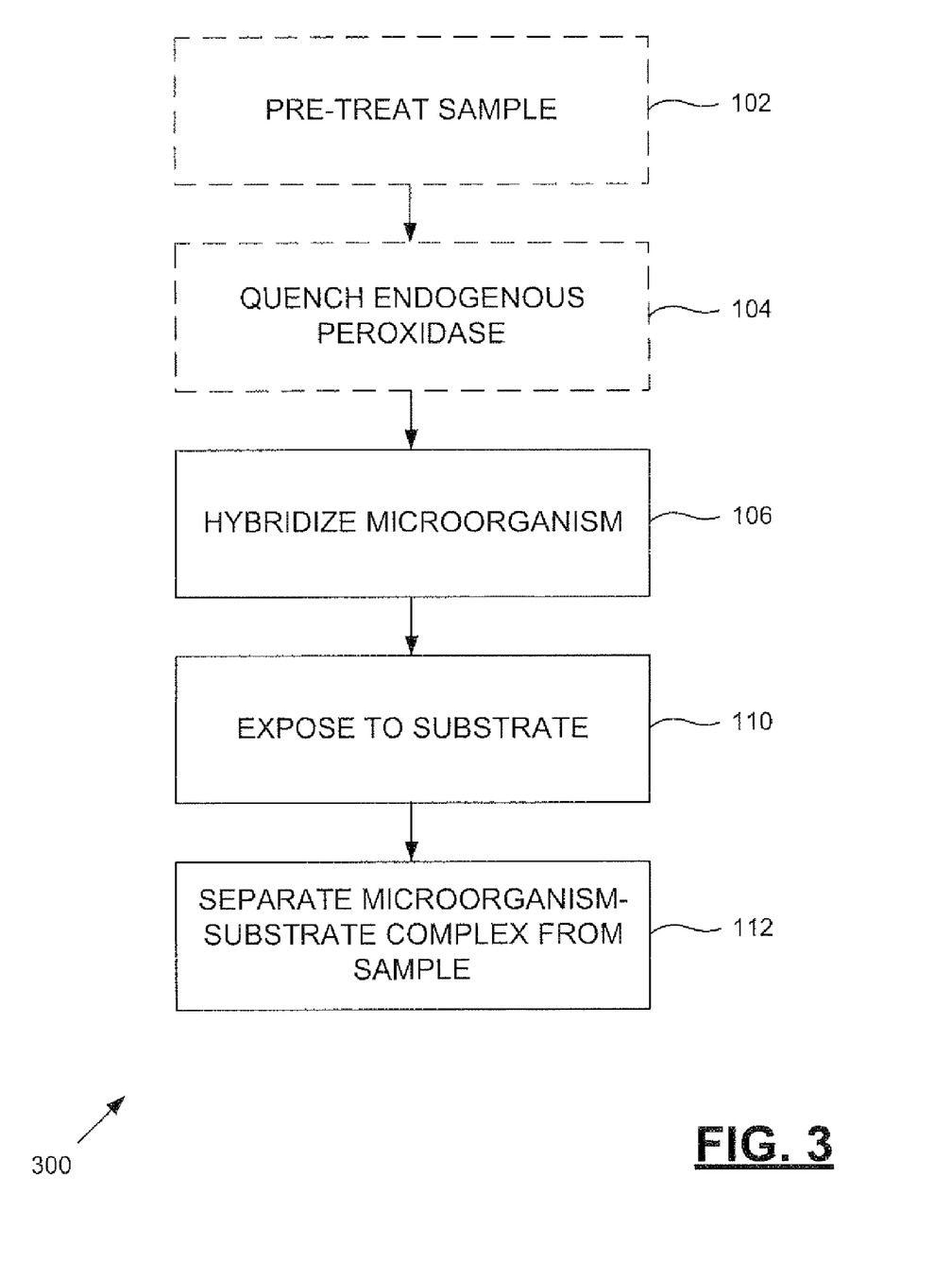
FIG. 3 is another flow diagram of another process of the invention.
Figure 4:
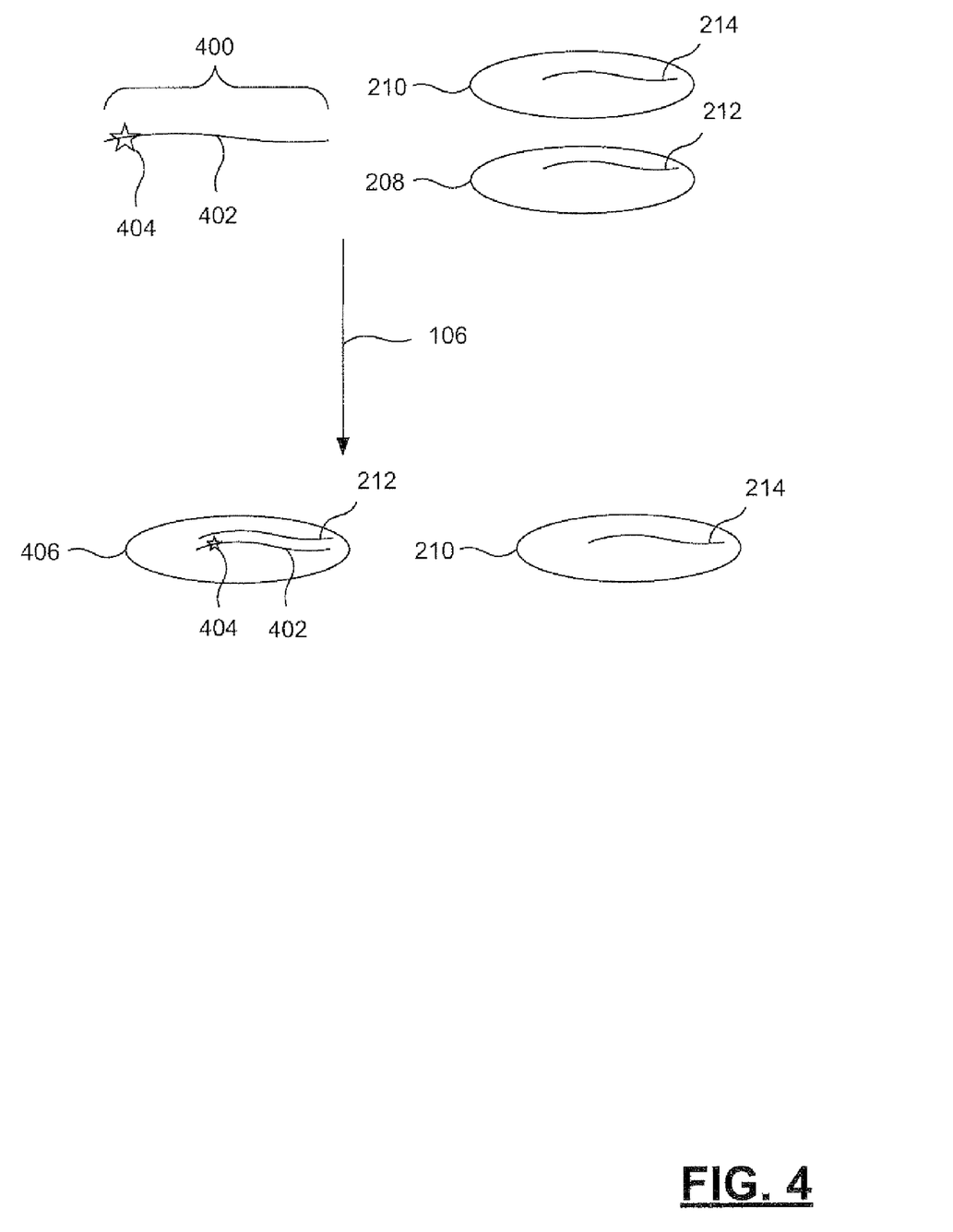
FIG. 4 is a graphic depiction of another embodiment of step 106 of the present invention.

FIG. 3 is a flow diagram of process 300 which is substantially similar to process 100 of FIG. 1. Process 300 differs from process 100 in that step 108 (exposing the hybridized substrate to an antigen) has been omitted. One method for omitting step 108 is to label the probe with an antigen, instead of with an enzyme. Reference may be had to FIG. 4.

FIG. 4 is a depiction of step 106 of process 300. As shown in FIG. 4, labeled probe 400 is comprised of probe 402 and label 404. In the embodiment depicted, label 404 is an antigen that does not need activation by an enzyme. Probe 402 is selected to hybridize to a nucleic acid sequence 212 of microorganism 208. Probe 402 does not hybridize to the nucleic acid sequence 214 of microorganism 210. After the execution of step 106, hybridized microorganism 406 is produced. Such a hybridized microorganism may then be exposed to a substrate coated with an antibody that is specific to antigen 404, as described in step 110. In another embodiment, not shown, the antigen is a hapten. As known in the art, a hapten is a type of antigen that elicits an immune response after being activated by a second (non-enzyme) molecule.

In another embodiment, not shown, the teachings of the present invention are used to purify a group of microorganisms from a sample, wherein the contaminates are environmental contaminates, rather than other microorganisms. In another embodiment, the organisms are separated based upon a common nucleic acid sequence that does not necessarily correspond to their species. For example, all microorganisms with a certain 16S rRNA sequence are isolated, but the probe is not designed to be species specific.

Example 1

Separation of ANME_2c Archaea from a Sample

Pre-treatment of sample—Eel river sediment samples were fixed with formaldehyde after sampling, flash frozen and stored at −80° C. At arrival in the lab, samples were thawed at room temperature, washed in 1×PBS, then in 1×PBS and 50% ethanol, re-suspended in absolute ethanol and stored at −80° C. until further processing. Two 1 ml sub-samples were mixed with 35 ml of 1× PBS containing 0.01 M Na-Pyrophosphate each, and subsequently sonicated on ice with two pulses of 10 seconds each. The slurry was centrifuged at 1000 g for 5 min at 4° C., re-suspended in 2 ml of 1× PBS and 50% ethanol, spun again at 500 g, re-suspended in 2 ml of absolute ethanol and stored at −20° C. until further processing. For permeabilization of the target cells, a 40 µl sub-sample of sonicated sediment was pipetted into 100 ml of 1× TE (10 mM TrisHCl, 1 mM EDTA, pH 9.0) in glass dish and microwaved in a histological microwave oven (Microwave Research & Applications, Inc., Laurel, Md., USA) at 65° C. for 2 min. Subsequently the slurry was put onto ice and centrifuged for 5 min at 1000 g at 4° C.

Quenching of endogenous peroxidase—To inactivate endogenous peroxidases, the pellet was re-suspended in 100 ml of 1×PBS containing 0.10% $H_2O_2$, vortexed, kept at room temperature for 1 min and centrifuged at 1000 g for 4 min to produce a pellet.

Hybridization of target cells—The pellet was re-suspended in 2 ml of hybridization buffer (60% formamide for ANME2c_760) and 20 µl of horseradish peroxidase labeled oligonucleotide probe. The specific probe used for the instant example was disclosed in *Applied & Environmental Microbiology*, Vol. 71, (January, 2005), pp. 467-479. This mix was then pipetted into a 2 ml reaction tube, placed into a 100 ml water bath and heated in a microwave oven at 46° C. for 30 min at a power output of 50%. The tube was gently mixed every 5 to 10 minutes during hybridization. Then, the hybridized sediment was mixed with 100 ml of 1×PBS, incubated at room temperature for 10 min and spun down at 1000 g for 5 min at 4° C.

Expose to antigen—The pellet was re-suspended in 5 ml of amplification buffer containing 0.0015% $H_2O_2$ and 0.5 µg Fluorescein labeled tyramide, 0.5 µg Biotin labeled tyramide (both custom labeled, for reference see) and incubated at 37° C. for 15 min. The biotin labeled tyramide served as an enhancer, as we observed a brighter and pH independent CARD-FISH signal for fluorescein-tyramide when biotin-tyramide has been added. The sediment was then mixed with 100 ml of 1×PBS, centrifuged at 1000 g for 5 min, re-suspended in 100 ml of 1×PBS containing 0.5% Bovine Serum Albumin (BSA) and microwaved 40° C. for 20 min. The sediment was then collected by centrifugation at 1000 g for 5 min, and re-suspended in 2 ml of 1×PBS containing 0.01 M Pyrophosphate and sonicated on ice for 15 sec.

Expose to antibody coated substrate—The CARD-FISH stained sediment sample was split into two 1 ml portions, 200 µl of BSA and 100 µl of Anti-Fluorescein-Antibody labeled paramagnetic beads (Dynal) were added to each portion, and both were incubated at room temperature for 1 hr on a rotator. To remove sediment particles and unbound cells and obtain a pure fraction of hybridized and captured target cells, we developed an apparatus consisting of two separation funnels. See FIG. 5. Here, funnel A is filled with 125 ml of 1×PBS.

Figure 5:
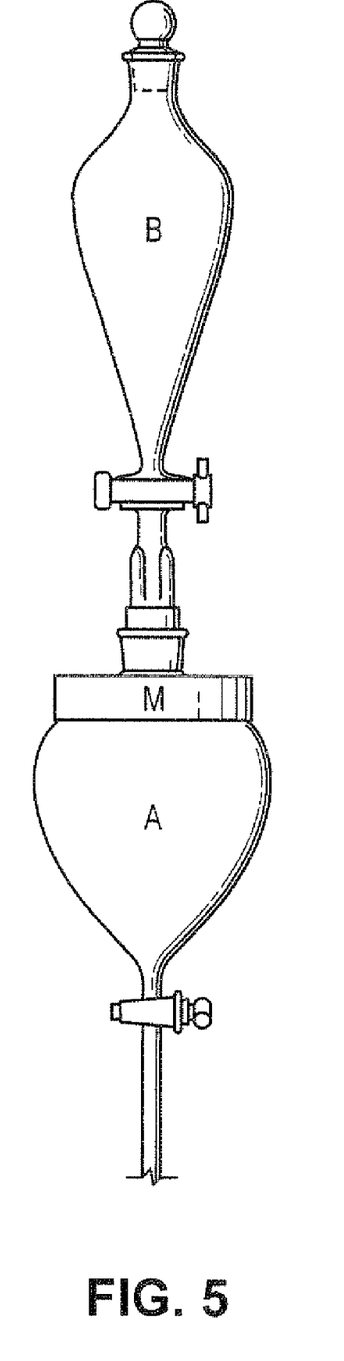
FIG. 5 is a schematic diagram of one apparatus for separating the microorganism-substrate complex from the sample.

After incubation with paramagnetic beads, the sediment slurry is pipetted into funnel A, a strong neodymium ring magnet M is set on top of funnel A. Funnel B, filled with 250 ml of 1×PBS is set onto of funnel A. The valves of both funnels are then opened to let PBS flow slowly from B to A, while the captured cells are always below the PBS level, preventing disturbance and loss of the target cells. Un-captured cells and sediment particles that are washed out during this procedure are again concentrated by centrifugation and again incubated with paramagnetic beads as described above. In the last step, funnel B is disconnected from funnel A, the PBS is drained so that the captured cells are now above the PBS level. To remove un-hybridized cells and particles that stick to the glass surface, the lower half of funnel A is rinsed repeatedly with PBS while the magnet is still applied. Then, the magnet is removed and the captured cells are re-suspended in 0.5 ml of 1× TE (10 mM TrisHCl, 1 mM EDTA, pH 9.0), and drained through the top opening of funnel A. Cells that still remained in funnel A are re-suspended with another 0.5 ml of TE.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A process for separating hybridized microorganisms from non-hybridized microorganisms comprising the steps of:
   a. hybridizing a microorganism of a plurality of microorganisms with an enzyme-labeled probe that hybridizes to a nucleic acid of the microorganism, to produce hybridized microorganisms and non-hybridized microorganisms;
   b. exposing the hybridized microorganisms to an antigen that is activated by the enzyme to produce labeled microorganisms;
   c. exposing the labeled microorganisms to a substrate that is coated with an antibody specific to the antigen to produce a bound microorganism-substrate complex; and
   d. separating the bound microorganism-substrate complex from the non-hybridized microorganisms.

2. The process as recited in claim 1, wherein the enzyme is a peroxidase.

3. The process as recited in claim 1, wherein the enzyme is a horseradish peroxidase.

4. The process as recited in claim 1, wherein the enzyme is a phosphatase.

5. The process as recited in claim 1, wherein the enzyme is selected from the group consisting of a glucose oxidase, a beta-galactosidase, and a urease.

6. The process as recited in claim 1, further comprising the step of pre-treating a raw sample which includes the plurality of microorganisms.

7. The process as recited in claim 1, further comprising the step of quenching an endogenous peroxidase.

8. The process as recited in claim 1, wherein the antigen is bound to a tyramide.

9. The process as recited in claim 1, wherein the antigen is a fluorescein.

10. The process as recited in claim 1, wherein the antigen is a biotin.

11. The process as recited in claim 1, wherein the antigen is a fluorescent dye.

12. The process as recited in claim 1, wherein the antigen is dinitrophenyl.

13. The process as recited in claim 1, wherein the antigen is digoxigenin.

14. The process as recited in claim 1, wherein the nucleic acid is a ribonucleic acid.

15. The process as recited in claim 1, wherein the nucleic acid is a ribosomal ribonucleic acid.

16. The process as recited in claim 1, wherein the nucleic acid is a messenger ribonucleic acid.

17. The process as recited in claim 1, wherein the nucleic acid is a chromosomal nucleic acid.

18. The process as recited in claim 1, wherein the nucleic acid is a plasmid nucleic acid.

19. The process as recited in claim 1, wherein the nucleic acid is a viral nucleic acid.

20. The process as recited in claim 1, wherein the substrate is a paramagnetic substrate.

21. The process as recited in claim 1, wherein the substrate is a magnetic substrate.

22. The process as recited in claim 1, wherein the substrate is a reaction tube.

23. The process as recited in claim 1, wherein the probe is a DNA probe.

24. The process as recited in claim 1, wherein the probe is a single stranded DNA probe.

25. A process for separating hybridized microorganisms from non-hybridized microorganisms comprising the steps of:
   a. hybridizing a species of microorganisms of a plurality of microorganisms in a raw sample with a labeled, DNA probe that hybridizes to a nucleic acid of the species of microorganisms, to produce hybridized microorganisms and non-hybridized microorganisms;
   b. exposing the hybridized microorganisms to a substrate that is coated with an antibody specific to the label producing a bound microorganism-substrate complex; and
   c. separating the bound microorganism-substrate complex from the non-hybridized microorganisms.

26. The process as recited in claim 25, wherein an endogenous peroxidase is present, and further comprising the step of quenching the endogenous peroxidase.

27. The process as recited in claim 25, wherein the label is a fluorescein.

28. The process as recited in claim 25, wherein the label is a biotin.

29. The process as recited in claim 25, wherein the label is a fluorescent dye.

30. The process as recited in claim 25, wherein the label is dinitrophenyl.

31. The process as recited in claim 25, wherein the label is digoxigenin.

32. The process as recited in claim 25, wherein the nucleic acid is a ribonucleic acid.

33. The process as recited in claim 25, wherein the nucleic acid is a ribosomal ribonucleic acid.

34. The process as recited in claim 25, wherein the nucleic acid is a messenger ribonucleic acid.

35. The process as recited in claim 25, wherein the nucleic acid is a chromosomal nucleic acid.

36. The process as recited in claim 25, wherein the nucleic acid is a plasmid nucleic acid.

37. The process as recited in claim 25, wherein the nucleic acid is a viral nucleic acid.

38. The process as recited in claim 25, wherein the substrate is a paramagnetic substrate.

39. The process as recited in claim 25, wherein the substrate is a magnetic substrate.

40. The process as recited in claim 25, wherein the substrate is a reaction tube.

41. The process recited in claim 25, wherein the label is a fluorescein labeled tyramide further comprising a second labeled probe which is a biotin labeled tyramide.

42. The process recited in claim 25, wherein the probe has from about 10 to about 200 base pairs.

43. The process recited in claim 25, wherein the probe has from about 10 to about 100 base pairs.

44. A process for separating hybridized microorganisms from non-hybridized microorganisms comprising the steps of:
   a. hybridizing a species of microorganisms of a plurality of microorganisms with an enzyme-labeled probe that hybridizes to a ribosomal ribonucleic acid of the species of microorganisms, to produce hybridized microorganisms and non-hybridized microorganisms;
   b. exposing the hybridized microorganisms to an antigen that is activated by the enzyme to produce labeled microorganisms;
   c. exposing the labeled microorganisms to a magnetic substrate that is coated with an antibody specific to the antigen to produce a bound microorganism-substrate complex; and
   d. separating the bound microorganism-substrate complex from the non-hybridized microorganisms.

45. A process for separating hybridized microorganisms from a sample comprising the steps of:
   a. hybridizing a microorganism with an enzyme-labeled probe that hybridizes to a nucleic acid of the microorganism, to produce a hybridized microorganism;
   b. exposing the hybridized microorganism to an antigen that is activated by the enzyme to produce a labeled microorganism;
   c. exposing the labeled microorganism to a magnetic substrate that is coated with an antibody specific to the antigen to produce a bound microorganism-substrate complex; and
   d. separating the bound microorganism-substrate complex from the sample.

\* \* \* \* \*